(12) United States Patent
Doms

(10) Patent No.: US 6,290,912 B1
(45) Date of Patent: Sep. 18, 2001

(54) READ HEAD FOR LUMINOMETER

(75) Inventor: Lutz Doms, Port Chester, NY (US)

(73) Assignee: Bayer Corporation, Tarrytown, NY (US)

( * ) Notice: Subject to any disclaimer, the term of this patent is extended or adjusted under 35 U.S.C. 154(b) by 0 days.

(21) Appl. No.: 09/339,619

(22) Filed: Jun. 24, 1999

Related U.S. Application Data

(60) Provisional application No. 60/092,771, filed on Jul. 14, 1998.

(51) Int. Cl.$^7$ .......................... G01N 21/29; G01N 21/27; G01N 21/00; G01N 15/06; B01L 3/00
(52) U.S. Cl. ..................................... 422/82.05; 422/82.08; 422/82.09; 422/99; 356/317; 356/318; 356/436; 250/564; 250/573
(58) Field of Search .............................. 422/82.05, 82.08, 422/82.09, 99; 356/436, 417, 318, 317

(56) References Cited

U.S. PATENT DOCUMENTS

| | | | |
|---|---|---|---|
| 4,121,466 | * | 10/1978 | Reichler et al. .................... 73/423 A |
| 4,312,341 | | 1/1982 | Zissimopoulos et al. . |
| 4,321,057 | * | 3/1982 | Buckles .............................. 23/230 B |
| 4,632,807 | * | 12/1986 | Marsoner ............................... 422/68 |
| 4,643,877 | * | 2/1987 | Opitz et al. ............................ 422/68 |
| 5,082,628 | * | 1/1992 | Andreotti et al. ................. 422/82.08 |
| 5,139,745 | * | 8/1992 | Barr et al. ......................... 422/82.05 |
| 5,268,167 | * | 12/1993 | Tung ..................................... 424/52 |
| 5,372,783 | * | 12/1994 | Lackie ................................. 422/68.1 |
| 5,399,497 | * | 3/1995 | Kumar et al. .......................... 436/53 |
| 5,714,388 | * | 2/1998 | Kusnetz ................................ 436/172 |
| 5,837,195 | * | 11/1998 | Malek et al. ........................... 422/52 |

FOREIGN PATENT DOCUMENTS 0 824 211  2/1998  (EP) .

OTHER PUBLICATIONS

European Search Report.

* cited by examiner

*Primary Examiner*—Jill Warden
*Assistant Examiner*—Brian R Gordon
(74) *Attorney, Agent, or Firm*—Andrew L. Klawitter, Esq.; Rodman & Rodman

(57) ABSTRACT

The read head for luminometer includes a housing that encloses a cylindrical core. The housing has a through opening that aligns with a central passageway of the cylindrical core to define a confinement space. The housing and the cylindrical core are formed in two parts that diverge or converge with respect to each other under the influence of a manually controlled actuator member. When the housing parts and the core parts are in a closed convergent position an analytical line that extends through the housing and the core is maintained in a confined position within the confinement space of the housing and the core. Actuation of the housing parts and the core parts into a diverged open position opens the confinement space that accommodates the analytical line. The analytical line can thus be lifted away from the previous confinement space or reinstalled back into the open confinement space and then locked in place by an actuation of the housing parts into a closed converged position along with the core parts. Installation or removal of the analytical line from the read head is thus accomplished in a direction that is perpendicular to the direction of the longitudinal axis of the confinement space.

10 Claims, 11 Drawing Sheets

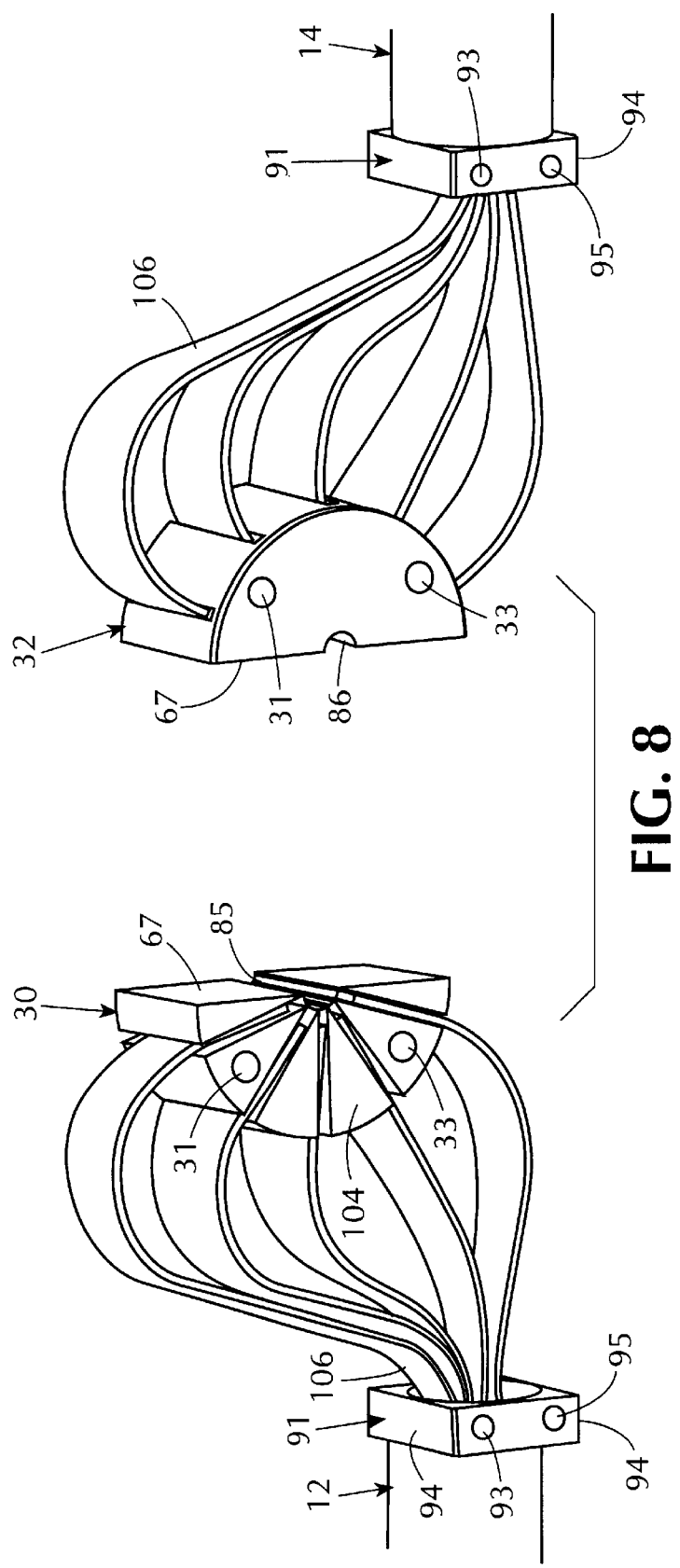

READ HEAD FOR LUMINOMETER

This Application claims benefit of Prov. No. 60/092,771 filed Jul. 14, 1998.

BACKGROUND OF THE INVENTION

This invention relates to sample analysis systems and more particularly to a novel read head for a luminometer employed in a sample analysis system, which read head permits easy installation and removal of an analytical line of the sample analysis system.

Automated sample analysis systems such as disclosed in U.S. Pat. Nos. 5,268,167 and 5,399,497 perform a variety of different tests on a test subject, such as a serum sample, in a relatively short period of time. The serum used in the disclosed sample analysis systems is divided into a series of sample segments that move through a transparent analytical line for analysis. Consecutive sample segments in the analytical line are segregated from each other by air spaces as described in U.S. Pat. No. 4,121,466.

One aspect of sample analysis includes providing respective sample segments with different reagents to produce reactions with analytes in the serum. These reactions are the basis for a battery of test information relating to the characteristics of the serum sample. During sample analysis the reaction between an analyte in a test sample segment and a reagent produces relatively low levels of light known as chemiluminescence.

A luminometer employs chemiluminescence to identify and quantify an analyte in a test sample segment. One type of luminometer as disclosed in U.S. Pat. No. 5,714,388 includes an apparatus for collecting and transmitting chemiluminescence. The disclosed collecting and transmitting apparatus includes a read head with a core that supports optic fibers at their free ends to form a central passageway of the core. A transparent analytical line, which houses moving test sample segments, extends through the central passageway of the core. When reacting segments in the analytical line move through the central passageway of the core, the chemiluminescence from such segments is transmitted through the transparent wall of the analytical line to the ends of the optic fibers in the core for detection and analysis at other portions of the luminometer.

Occasionally the analytical line, which can be several meters long, must be removed from the read head to permit repair or replacement of the read head or the analytical line. Line removal is typically accomplished by snaking the analytical line through the central passageway of the read head core, which can be a tedious, time consuming and expensive operation.

It is thus desirable to provide a read head for a luminometer which permits removal of an analytical line from the read head without the need to snake the analytical line through the read head. It is also desirable to provide a read head that can be easily opened and closed to permit quick and simple installation and removal of an analytical line.

OBJECTS AND SUMMARY OF THE INVENTION

Among the several objects of the invention may be noted the provision of a novel read head, a novel read head including a housing and a core that permits easy installation and removal of an analytical line, a novel read head with a through opening that can be split to facilitate removal of an analytical line, a novel read head including a housing in two sections, a novel read head with a core in two half sections that are respectively secured to two sections of a read head housing, a novel read head wherein two sections of a housing and two sections of a core are convergeable toward each other to a closed position to secure an analytical line and are divergeable away from each other to an open position to permit removal or installation of an analytical line, and a novel read head with an actuator to actuate simultaneous converging movement or diverging movement of two housing sections and two core sections to permit installation and removal of an analytical line from the read head.

Other objects and features of the invention will be in part apparent and in part pointed out hereinafter.

In accordance with the invention, a read head for a luminometer includes a housing that encloses a cylindrical core. The housing has a through opening that aligns with a central passageway of the cylindrical core.

The housing is composed of a pair of housing portions pivotally joined together at a pivot member to permit converging and diverging movement of the housing portions about the pivot member. The housing portions are thus divergeable away from each other a predetermined amount to a predetermined open position and convergeable from the open position to a closed limit position.

The through opening in the housing is sized to confine an elongated analytical line, preferably formed of a flexible transparent plastic material. Serum segments that are being tested in a sample analysis system move within the analytical line through the read head.

Sections of the through opening in the read head housing are located in each housing portion. Thus when the housing portions are diverged to the predetermined open position the through opening splits into two spaced through opening sections. The analytical line can then be installed (dropped in) or removed (lifted out) from the two spaced through opening sections in a direction perpendicular to the direction of a longitudinal axis of the through opening.

Each of the housing portions are in the form of a hollow shell. The cylindrical core is formed in two sections with one of the core sections being mounted within one of the housing shells and the other core section being mounted within the other housing shell. The core sections define the central passageway that aligns with the through opening of the housing. The core sections are in a closed limit position when the housing portions are in their closed limit position. The central passageway of the core and the through opening of the housing thus confine and secure an analytical line therein when the housing portions are in the closed limit position.

The core sections are also divergeable away from each other when the housing portions are diverged from each other. Each of the core sections includes a section of the central passageway such that divergence of the core sections splits the central passageway into two spaced passageway sections. When the housing portions and the core sections are in their diverged open position the analytical line can be installed in or removed from the two spaced passageway sections of the core and the two spaced through opening sections of the housing in a direction that is perpendicular to the direction of the longitudinal axis.

In a preferred embodiment of the invention the pivot member is also supported on a support member outside the housing such that the housing portions are convergeable and divergeable relative to the support member. Actuator means are provided on the support member and the housing for actuating simultaneous converging movement or diverging movement of the housing portions relative to the support member.

The actuating means includes a moving means engageable with the housing portions for simultaneously converging or diverging the housing portions, and an actuator member for actuating movement of the moving means. The moving means include a pair of motion transfer members, with one of the motion transfer members being fixed to one of the housing portions and the other motion transfer member being fixed to the other housing portion. The moving means further include a moving member that is movable in opposite directions with respect to the housing portions, such as upwardly and downwardly with respect to the housing portions. The moving member is engageable with the motion transfer members such that movement of the moving member causes simultaneous movement of each of the motion transfer members and corresponding converging or diverging movement of the housing portions in response to the direction of movement of the moving member.

In a preferred embodiment of the invention the motion transfer members include a pin projecting from each of the housing portions and the moving member includes a bar with a horizontal slot formed at each end of the bar to permit sliding engagement of the bar relative to the pins. Thus movement of the bar in opposite directions upwardly and downwardly against the pins causes converging or diverging movement of the housing portions in response to the direction of movement of the bar.

The actuator member in the preferred embodiment of the invention includes a captive screw having one end held captive relative to the housing portions while being threadably engaged in the moving member. Thus rotation of the captive screw in one direction causes vertical movement of the moving member in one direction and reverse rotation of the captive screw causes vertical movement of the moving member in the opposite direction.

The actuating means further include a stabilizing member that is immovable with respect to the housing portion and extends through the moving member such that the moving member is movable in a vertical direction relative to the stabilizing member. In a preferred embodiment of the invention the stabilizing member is in the form of a vertical pin or rod that guides and stabilizes the vertical movement of the moving member by the captive screw.

The invention accordingly comprises the constructions hereinafter described, the scope of the invention being indicated in the claims.

DESCRIPTION OF THE DRAWINGS

In the accompanying drawings,

FIG. 8 is a simplified perspective view of core sections of the read head including associated fiber optic ribbons that merge into respective conduit sections;

Corresponding reference numbers indicate corresponding parts throughout the several views of the drawings.

DETAILED DESCRIPTION OF THE INVENTION

Figure 1:
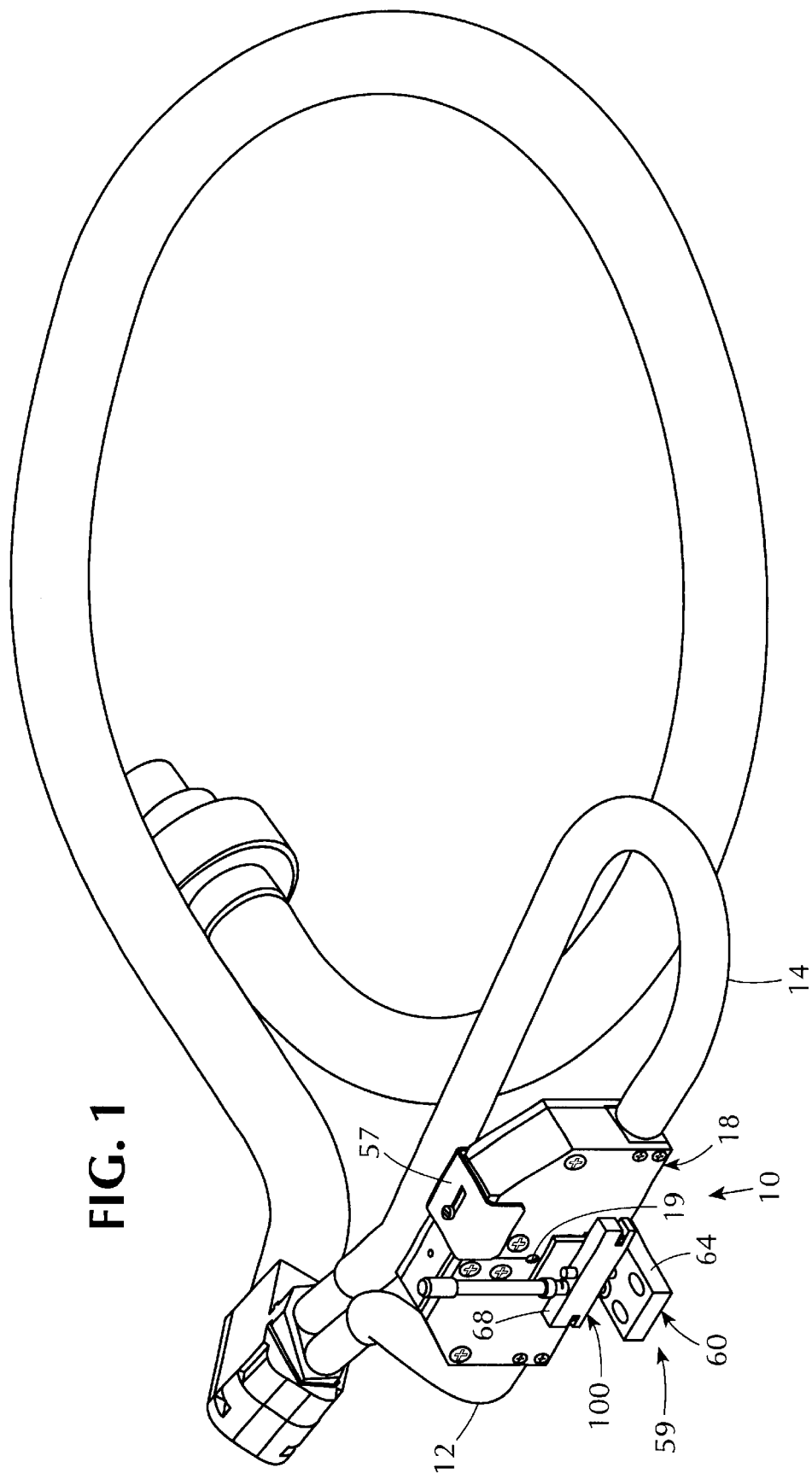
FIG. 1 is a simplified perspective view of a read head for a luminometer incorporating the present invention, the read head being shown with associated fiber optic ribbon conduits.

Referring to the drawings, a read head incorporating one embodiment of the invention is generally indicated by the reference number 10 in FIG. 1.

Figure 2:
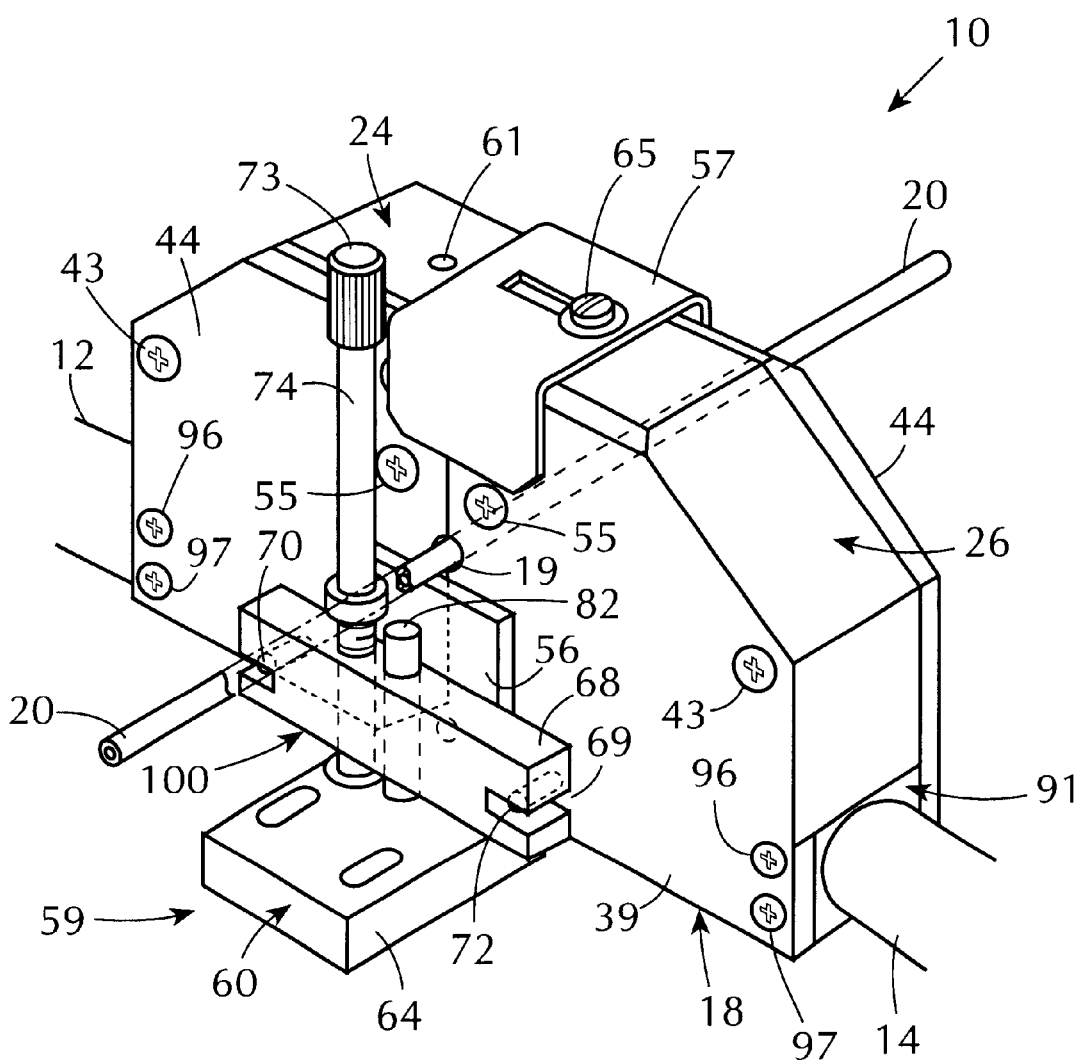
FIG. 2 is an enlarged perspective view of the read head in a closed position and with an analytical line installed therein.
Figure 3:
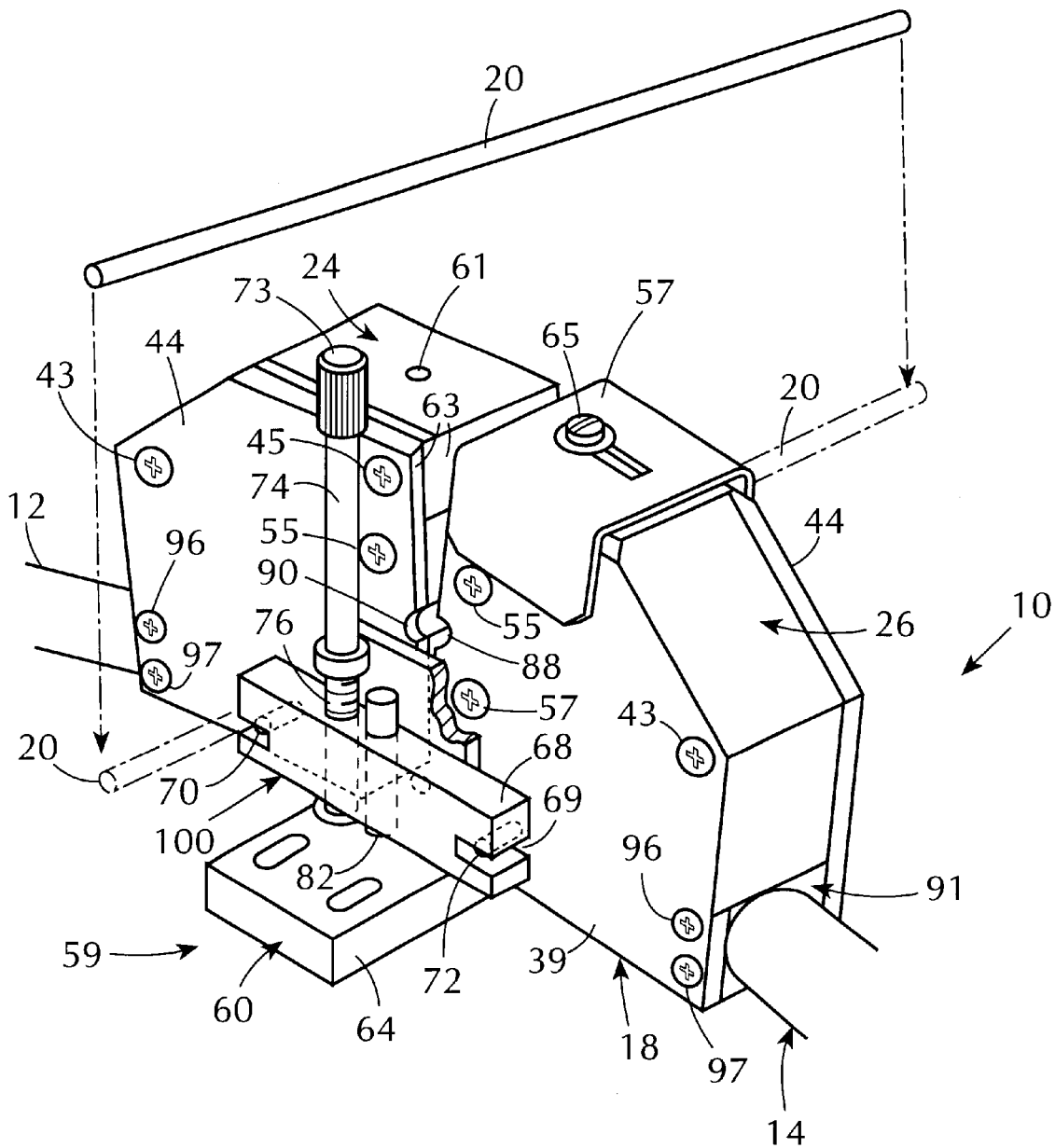
FIG. 3 is a view similar to FIG. 2 with the read head in an open position permitting installation and or removal of the analytical line.
Figure 6:
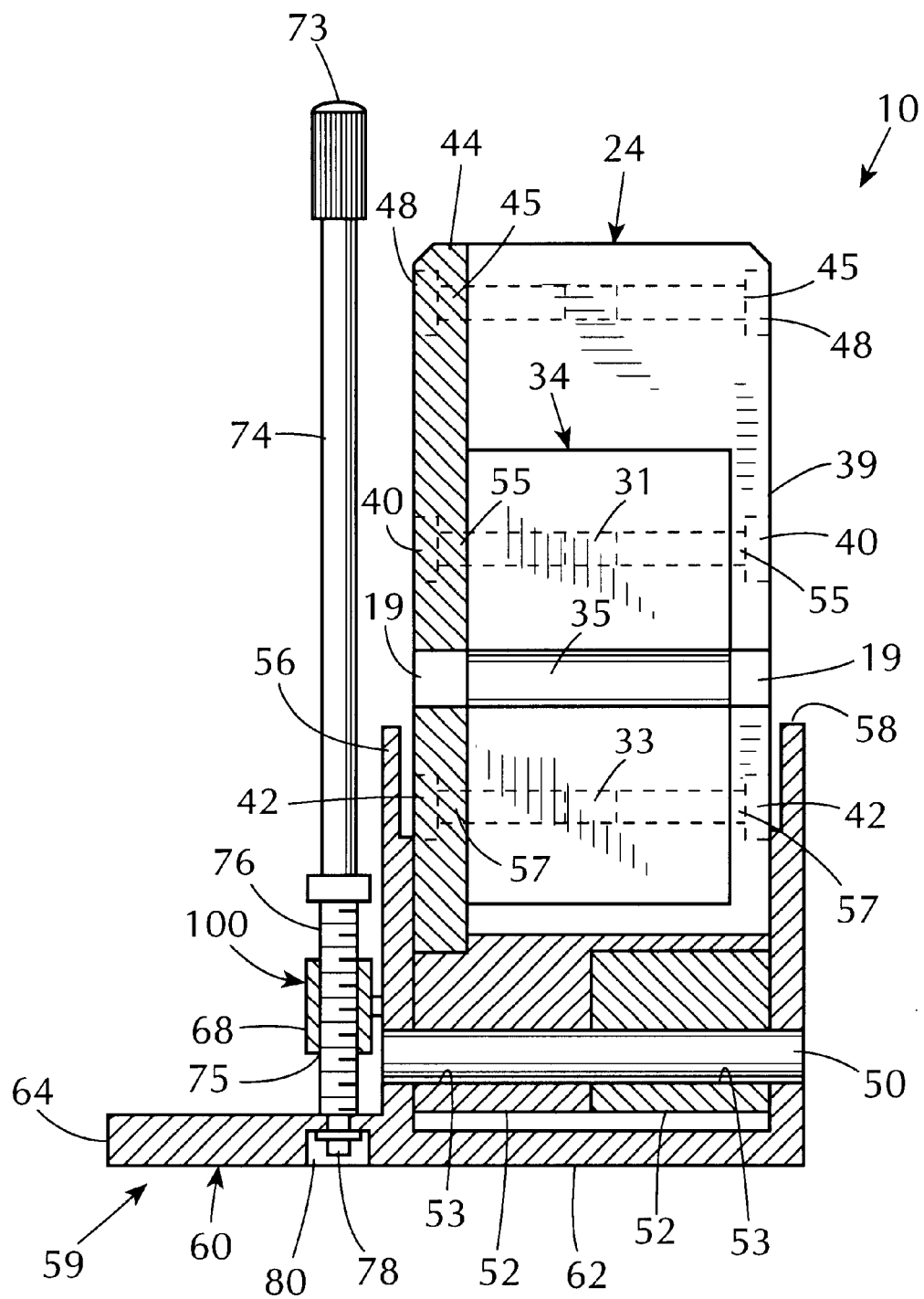
FIG. 6 is a sectional view thereof taken on the line 6—6 of FIG. 5.
Figure 7:
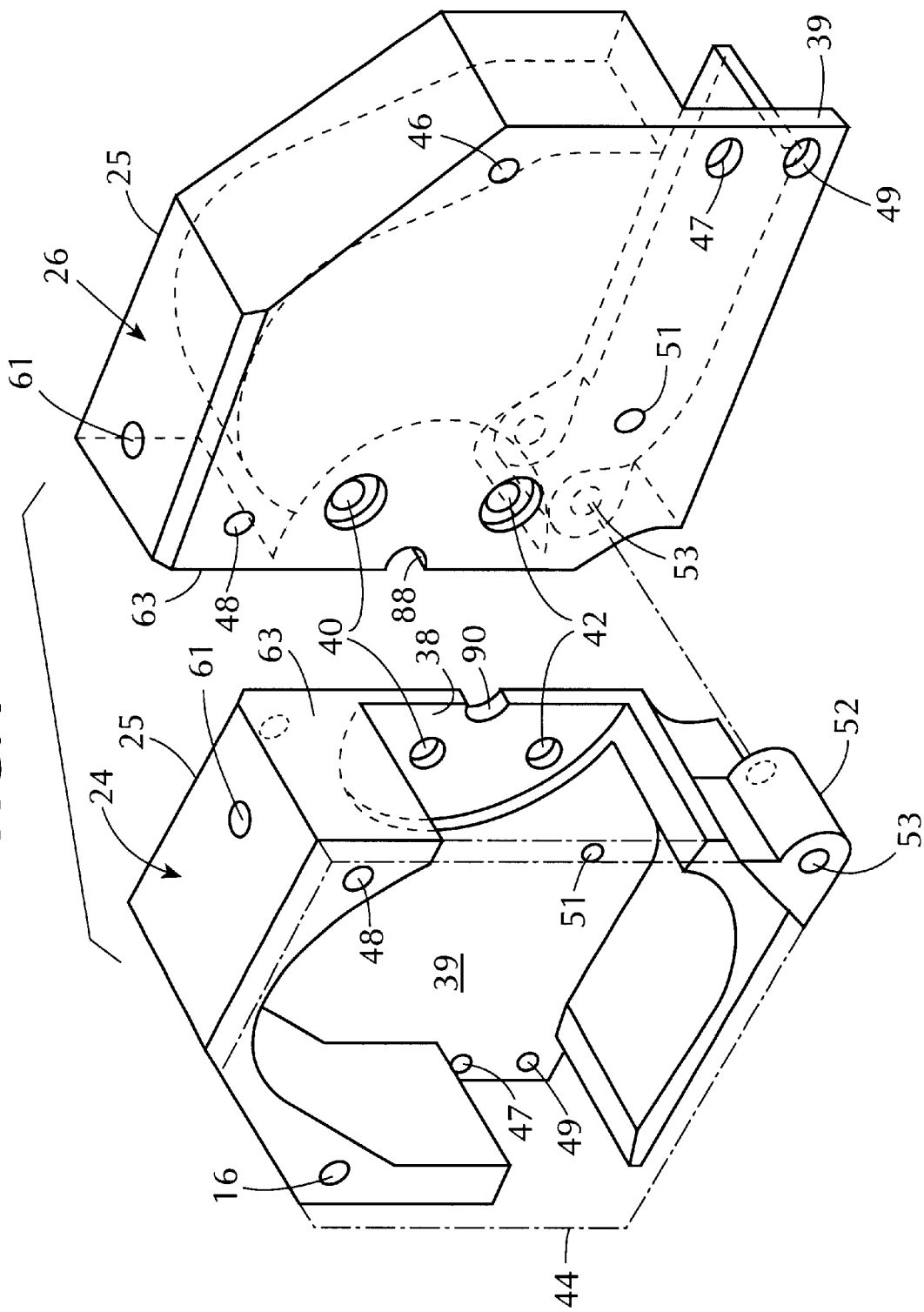
FIG. 7 is a perspective view of housing portions of the read head with a cover plate of one housing portion shown in phantom outline.
Figure 10:
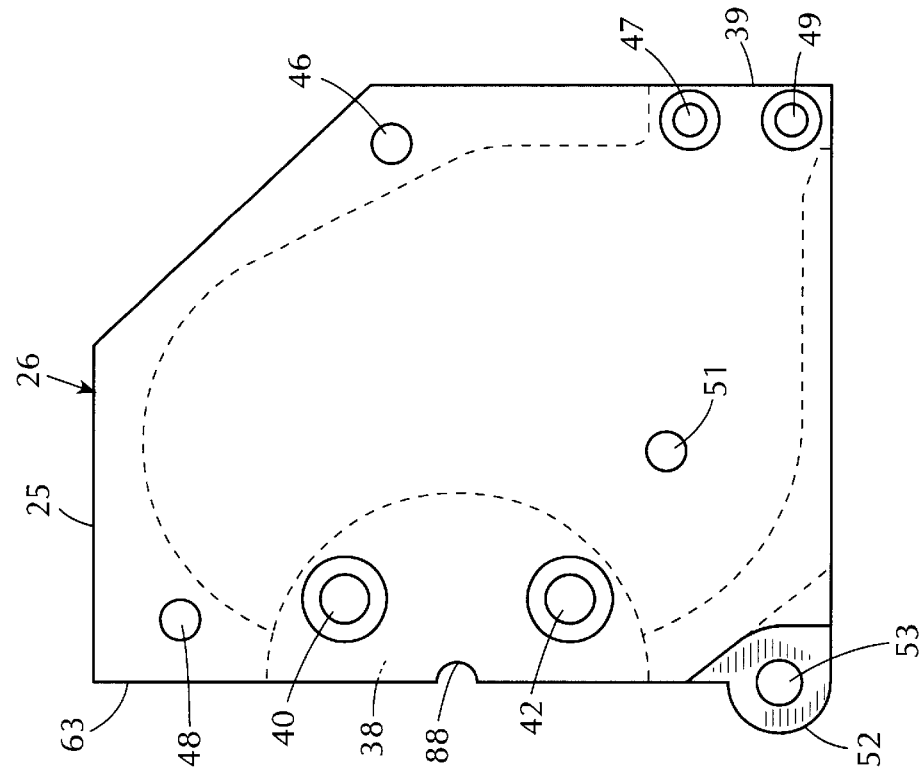
FIGS. 9 and 10 are front views of the respective housing portions shown in FIG. 7.
Figure 9:
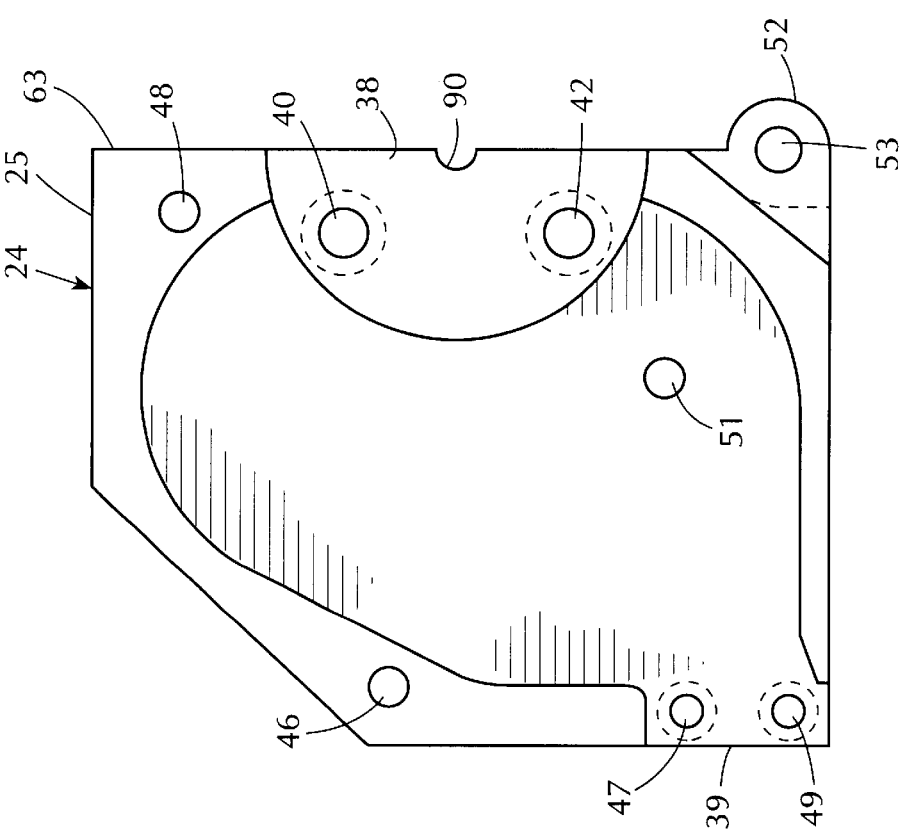

The read head 10 includes a light proof opaque housing 18 (FIG. 1) having a through opening 19 to confine an analytical line 20 (FIG. 2). The housing 18 also includes a hollow space 28 (FIG. 5) for accommodation of a generally cylindrical core 34. The housing 18 is composed of housing portions 24 and 26 (FIGS. 2 and 3) of identical construction and preferably formed of blackened anodized aluminum. Each of the housing portions 24 and 26 include a one-piece molded chamber section 25 (FIG. 7) and a cover plate 44 (FIGS. 3 and 6). FIGS. 7, 9 and 10 indicate the housing portion reference numbers 24 and 26 associated with the respective chamber sections 25, 25.

The chamber sections 25, 25 (FIG. 7) each include fastener openings 40 and 42 for core securement, fastener openings 46 and 48 for cover plate securement, fastener openings 47 and 49 for conduit securement, and a pin receiving opening 51 for pin attachment. Corresponding aligned openings as shown in FIG. 6 are provided in each cover plate 44.

The core 34 has a central passageway 35 (FIGS. 5 and 6) that aligns with the housing through opening 19. The core 34 is composed of two semi-cylindrical core sections 30 and 32 (FIGS. 5 and 8) that have threaded openings 31 and 33. The core sections 30 and 32 are respectively installed in semi-circular depressions, 38, 38, (FIG. 7) formed in a wall 39 of each chamber section 25. Fasteners 55 and 57 (FIGS. 3 and 6) pass through the openings 40 and 42 in each chamber section 25, the corresponding aligned fastener openings in the cover plate 44 and the core openings 31 and 33 to secure the respective core sections 30 and 32 to the respective housing portions 24 and 26.

The cover plate 44 is further secured to the each of the chamber sections 25, 25 by fasteners 43 and 45 (FIG. 3) that engage the openings 46 and 48 (FIG. 7) in the chamber sections 25, 25. Corresponding fasteners 43 and 45 can also be provided in the openings 46 and 48 at the wall 39 of the chamber sections 25, 25.

Figure 11:
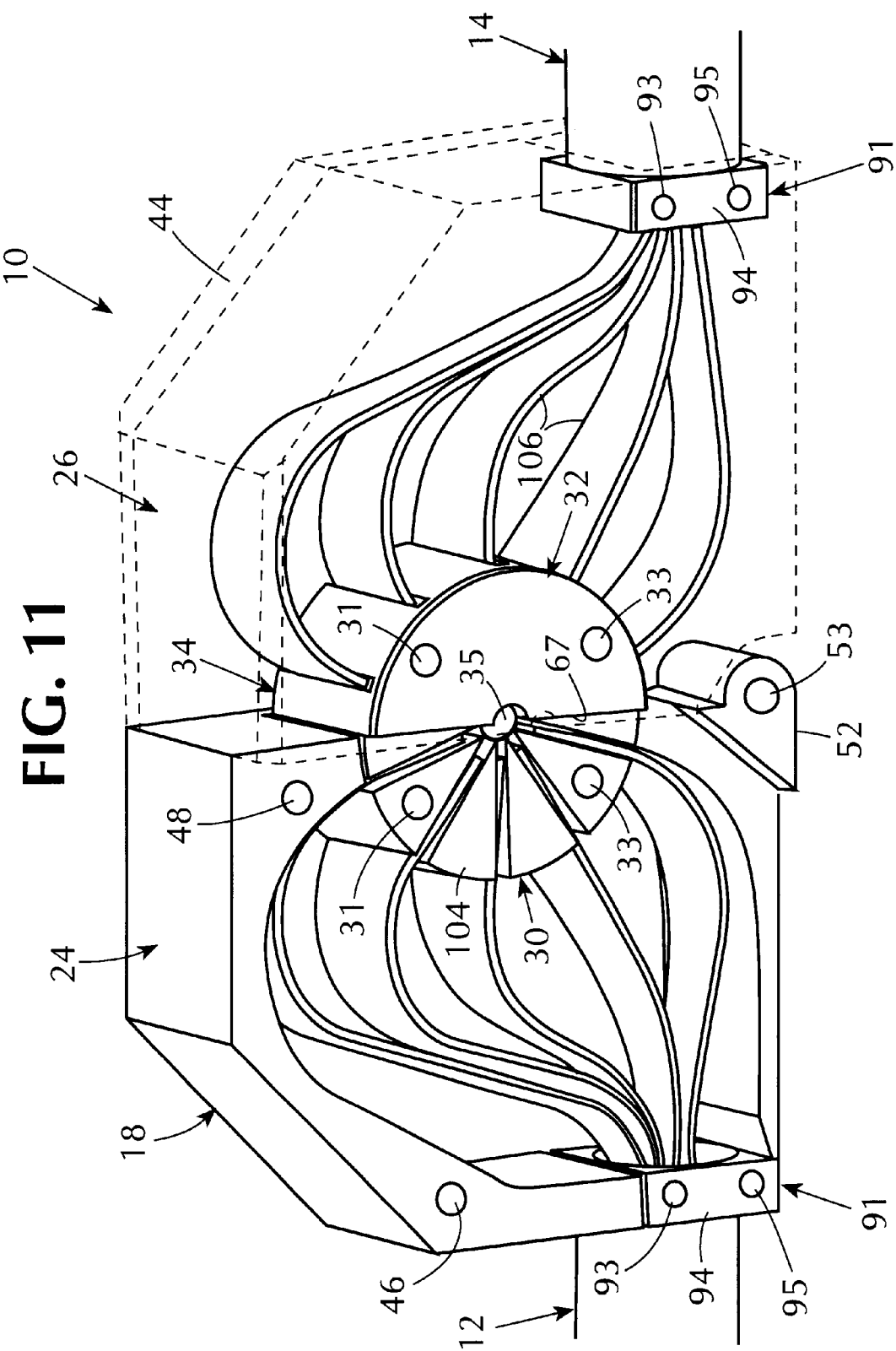
FIG. 11 is a simplified perspective view of the read head in a closed position with the cover plate of one housing portion omitted and the other housing portion being shown in phantom outline.
Figure 12:
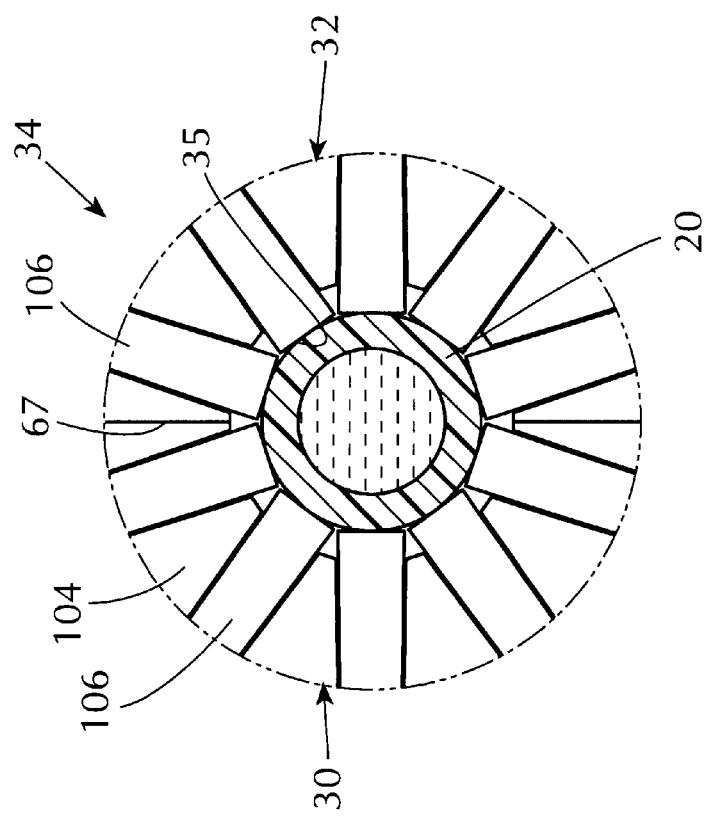
FIG. 12 is a sectional view of the read head core in a closed position to define the central passageway for the analytical line and including the fiber optic ribbons; and, FIG. 13 is an enlarged fragmentary detail of the central portion of the read core in closed position with the analytical line shown in section in the central passageway.

The semi-cylindrical core sections 30 and 32 include angular segments 104 (FIGS. 11, 12 and 13) and fiber optic ribbons 106 sandwiched between adjacent angular segments 104. The fiber optic ribbons 106 extend from the central passageway 35 and beyond the periphery of the core sections 30, 32 to form fiber optic bundles that are housed in fiber optic ribbon conduits 12 and 14. The fiber optic ribbon conduits 12 and 14 extend from opposite ends of the housing 18 to transfer light produced by sample reactions in the analytical line 20 (FIGS. 2, 3 and 13) to a light measuring device (not shown). U.S. Pat. No. 5,714,388 discloses the construction details of a cylindrical core, and the teachings of U.S. Pat. No. 5,714,388, incorporated by reference herein, are adaptable to the construction of the semi-cylindrical core sections 30 and 32 of the core 34.

The core sections 30 and 32 are installed in the housing portions 24 and 26, and the housing portions 24 and 26 are mounted on a pivot rod 50 (FIG. 6). The pivot rod 50 passes through pivot rod openings 53, 53 (FIG. 6) formed in pivot hinge portions 52 (FIG. 7) on each chamber section 25, 25. There is no corresponding pivot rod opening in the cover plates 44, 44. Opposite end portions of the pivot rod 50 are supported in opposite wall portions 56 and 58 of a support means 59 that includes a support member or cradle member 60. The cradle member 60 has a base portion 62 (FIG. 6) with a base flange 64 that extends from the base portion 62.

Under this arrangement the housing portions 24 and 26, with their respective core sections 30 and 32, can diverge away from each other and converge toward each other about the pivot rod 50 relative to the cradle member 60. The housing portions 24 and 26 can be locked in a closed position by a U-shaped closure plate 57 (FIGS. 2 and 3) that is slideably mounted on the housing portion 26 for movement over the housing portion 24. A lock screw 65 threaded into an opening 61 of the housing portion 26 (FIG. 5) locks and releases the closure plate 57. The threaded opening 61 in the housing portion 24 need not have a corresponding screw but is blocked or filled in any suitable known manner.

The housing portions 24 and 26 have confronting or parting surfaces 63, 63 (FIGS. 3 and 7) at the chamber sections 25, 25 and at a vertical parting or confronting edge of each cover plate 44, as most clearly shown in FIG. 3. The through opening 19 includes a through opening section 90 (FIGS. 3 and 7) at the confronting surface 63 of the housing portion 24 and a through opening section 88 at the confronting surface 63 of the housing portion 26.

The core sections 30 and 32 have confronting or parting surfaces 67, 67 (FIG. 8). The passageway 35 includes a passageway section 85 at the confronting surface 67 of the core section 30, and a passageway section 86 at the confronting surface 67 of the core section 32.

Figure 5:
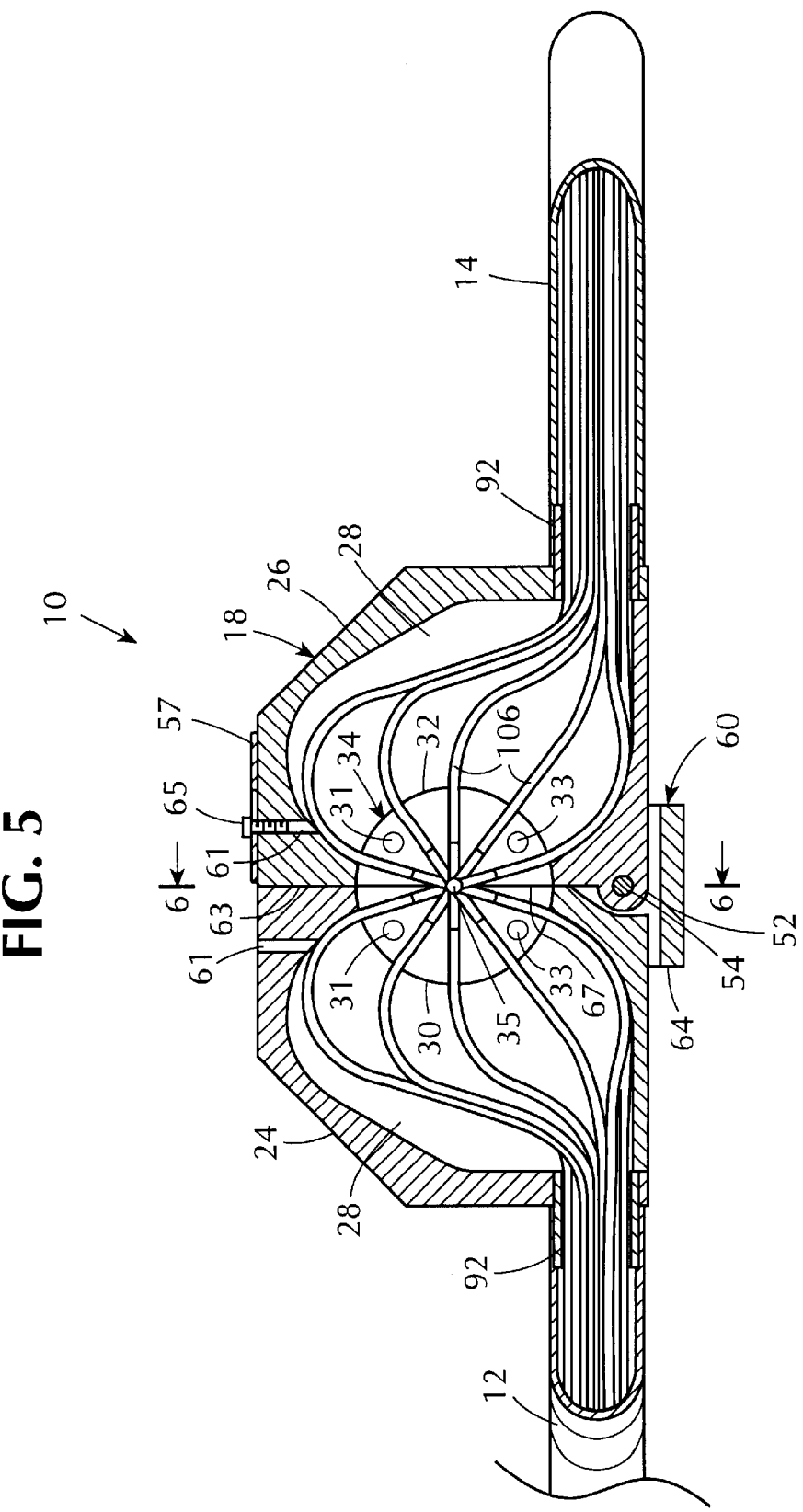
FIG. 5 is a sectional view thereof taken on the line 5—5 of FIG. 4.

When the housing portions 24 and 26 are in the closed position (FIG. 2) the confronting surfaces 63, 63 (FIGS. 9 and 10) of the housing portions abut against each other as most clearly shown in FIG. 5 to define a closed limit position. The confronting surfaces 67, 67 (FIG. 8) of the core sections 30 and 32 also abut each other when the housing portions 24 and 26 are in the closed limit position. Thus the core sections 30 and 32 are also in a closed position that defines the unified cylindrical form of the core 34 when the housing portions 24 and 26 are in the closed limit position.

Figure 13:
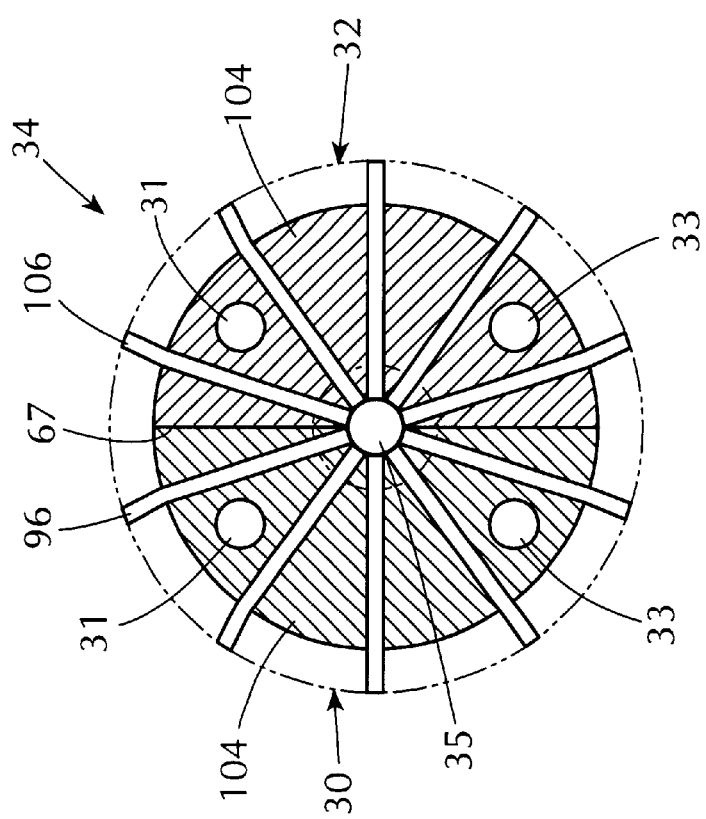

When the housing portions 24 and 26 are in the closed limit position and the core sections 30 and 32 are in the closed position the analytical line 20 is surrounded by the through opening 19 of the housing 18 and the central passageway 35 of the core 34 (FIG. 13).

Figure 4:
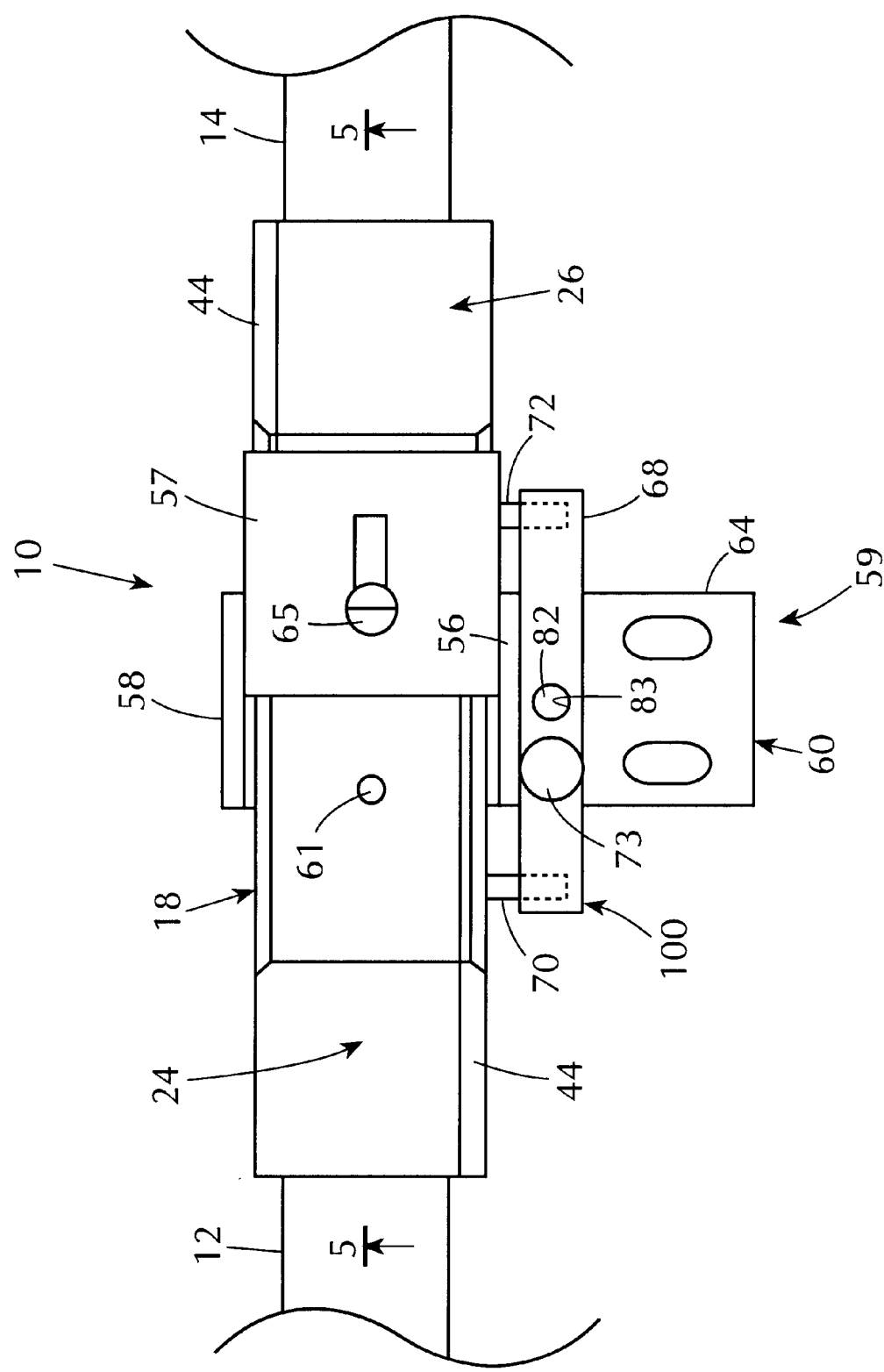
FIG. 4 is a top view thereof with the analytical line omitted.

The read head 10 further includes actuating means 100 on the cradle member 60 and the housing 18. The actuating means 100 includes a balance bar or moving member 68 that is elongated in the horizontal direction as shown in FIGS. 2 and 3. The moving member 68, includes a horizontal slot 69 at each opposite end formed to engage respective force transfer pins 70 and 72. The force transfer pins 70 and 72 are fixed in an opening 51, 51 of each housing portion 24, 26 but project from only one side of the housing 18 as most clearly shown in FIG. 4.

Thus the force transfer pins 70 and 72 respectively project from the cover plate 44 of the housing portion 24 and from the wall portion 39 of the housing portion 26. Corresponding openings 51, 51 in the other side of the housing 18 are filled in any suitable known manner.

The moving member 68 includes a vertical threaded opening 75 (FIG. 6) for reception of an actuator member or control rod 74 (FIG. 2) with a finger gripping portion 73 at an upper free end of the rod 74 and an opposite end portion 78. The control rod 74 (FIG. 6) also has a threaded portion 76 in the threaded opening 75 of the moving member 68, with the end portion 78 being held captive in a recess 80 of the base flange 64.

The moving member 68 is provided with a stabilizing pin 82 alongside and parallel to the control rod 74 (FIG. 2). The stabilizing pin 82 has one end fixed to the base flange 64 and extends vertically through an opening 83 in the moving member 68 such that the moving member 68 is slideable in a vertical direction with respect to the stabilizing pin 82.

Under this arrangement rotation of the control rod 74 at the finger gripping portion 73 can raise or lower the moving member 68 along a vertical path controlled by the control rod 74 and the stabilizing pin 82.

The read head 10 is thus adjustable to permit drop-in installation or lift-out removal of the analytical line 20. To permit adjustment of the read head 10 to an open position that permits installation or removal of the analytical line 20 the closure plate 57 (FIGS. 2 and 3) is first loosened by loosening the lock screw 65. The closure plate 57 is then slid from the locked position of FIG. 2 to the unlocked position of FIG. 3. The control rod 74 is turned in a direction that raises the moving member 68. The rising moving member 68 exerts an upward force on the force transfer pins 70 and 72, which function as motion transfer members, to cause the housing portions 24 and 26 to diverge about the pivot rod 50 relative to the cradle member 60.

Divergence of the housing sections 24 and 26 splits the through opening 19 into the two semi-circular through opening sections 88 and 90 that become spaced from each other (FIGS. 2 and 3). Divergence of the housing portions 24 and 26 also diverges the core sections 30 and 32 thereby splitting the central passageway 35 into the two semi-cylindrical passageway sections 85 and 86 (FIG. 8) that become spaced from each other. The analytical line 20 can thus be easily dropped into or lifted away from the split sections 88, 90 of the through opening 19 and the split sections 85, 86 of the central passageway 35 (FIG. 6).

Lift-away removal or drop-in installation of the analytical line 20 is in a direction perpendicular to the direction of the longitudinal axis of the through opening 19. The longitudinal axis of the through opening 19 extends in the same direction as the analytical line 20 when the analytical line 20 is confined in the housing 18 and the core 34.

While the precise dimensions of the analytical line 20, the through opening 19 of the housing 18, and the central passageway 35 of the core 34 can vary depending upon the outside diameter of the analytical line 20 an example of suitable dimensions for these structures and structural features include an outside diameter of approximately 2.870 millimeters for the analytical line 20, a diameter of approximately 3.0 millimeters for the through opening 19 of the housing 18 and a diameter of approximately 3.4 millimeters for the central passageway 35 of the core 34.

Light proofjunction members such as 91 (FIGS. 2 and 3) are provided at the housing sections 24 and 26 where the conduits 12 and 14 exit from such housing sections. The junction members 91, 91 include a tubular support 92 (FIG. 5) for the conduits 12 and 14 combined with a plate or baffle member 94 (FIG. 8) having threaded openings 93 and 95. The threaded openings 93 and 95 align with the openings 47 and 49 in the chamber sections 25, 25 and the corresponding aligned openings in each cover plate 44. The junction members 91, 91 are held in place by fasteners 96 and 97 (FIGS. 2 and 3) that pass through the openings 47 and 49 to engage the openings 93 and 95 of the baffle member.

Some advantages of the present invention evident from the foregoing description include a read head for a luminometer that can be easily opened and closed to permit drop-in installation and lift-away removal of an analytical line from the read head, a read head that can be easily opened and closed by simply turning or adjusting a single adjustment member, and a read head that permits simple installation of a core with associated fiber optic conduits. Further advantages are a read head housing that is simply constructed of two different parts, namely, the chamber section 25 and the cover plate 44, which are assembled to form each of the housing portions 24 and 26. A further advantage is that the read head can be easily assembled and disassembled, and easily opened and closed without the need for special skills or extensive training.

In view of the above, it will be seen that the several objects of the invention are achieved and other advantageous results attained.

As various changes can be made in the above constructions without departing from the scope of the invention, it is intended that all matter contained in the above description or shown in the accompanying drawings shall be interpreted as illustrative and not in a limiting sense.

What is claimed is:

1. In a read head for a luminometer comprising, a housing that supports a free end portion of optic fibers, and supports a transparent analytical line, which transparent analytical line houses moving test sample; wherein luminescence from said sample is transmitted though the transparent analytical line to the free end portion of the optic fibers for detection and analysis by the luminometer, the improvement comprising,
   a) a housing having a through opening with a longitudinal axis,
   b) said housing including a pair of housing portions,
   c) pivot means for joining said housing portions together to permit converging and diverging movement of said housing portions about said pivot means such that said housing portions are divergable away from each other a predetermined amount to a predetermined open position, and convergable from said open position to a closed limit position, and
   d) said through opening being sized to confine an elongated analytical line when said housing portions are in said closed limit position, and said through opening being positioned in said housing portions to split into two spaced through opening sections upon divergence of said housing portions to said predetermined open position, thereby permitting removal of said analytical line from the two spaced through opening sections in a direction perpendicular to the direction of said longitudinal axis.

2. The read head as claimed in claim 1 further including means for actuating said converging and diverging movement of said housing portions.

3. The read head as claimed in claim 2 wherein said actuating means includes moving means engageable with said housing portions for simultaneously converging or diverging said housing portions, and an actuator member for actuating movement of said moving means.

4. The read head as claimed in claim 3 wherein said moving means include a pair of motion transfer members, one said motion transfer member fixed to one of said housing portions, the other said motion transfer member fixed to the other said housing portion, said moving means further including a moving member movable in opposite directions with respect to said housing portions, said moving member being engageable with said motion transfer members such that movement of said moving member causes simultaneous movement of each of said motion transfer members and corresponding converging or diverging movement of said housing portions in response to the direction of movement of said moving member.

5. The read head as claimed in claim 4 wherein said motion transfer members include a pin projecting from each of said housing portions, and said moving member includes a bar with a horizontal slot formed at each end of the bar to permit sliding engagement of the bar relative to said pins such that movement of said bar in said opposite directions against said pins causes converging or diverging movement of said housing portions in response to the direction of movement of said bar.

6. The read head as claimed in claim 3 wherein said moving means includes a moving member movable with respect to said housing portions and said actuator member includes a captive screw having one end held captive relative to said housing portions, said captive screw being threadably engaged in said moving member such that rotation of said captive screw in one direction causes translating movement of said moving member in one of said opposite directions, and rotation of said captive screw in another direction causes translating movement of said moving member in the other of said opposite directions.

7. The read head as claimed in claim 6 wherein said actuating means further includes a stabilizing member immovable with respect to said housing portions and extending through said moving member such that said moving member is movable relative to said stabilizing member, said stabilizing member guiding and stabilizing the movement of said moving member by said captive screw.

8. The read head as claimed in claim 1 wherein each said housing portion is in the form of a hollow shell, a cylindrical core is disposed within said hollow shells, said cylindrical core being formed in two sections, one said section of the core being mounted within said housing shell and the other said section of the core being mounted within the other said housing shell, said core sections defining a central passageway in alignment with said through opening to confine an analytical line in said central passageway when said housing portions are in said closed limit position, said core sections being divergable away from each other when said housing portions are diverged from each other, and wherein said central passageway is positioned such that divergence of said core sections splits said central passageway into two spaced passageway sections, to permit removal of said analytical line from said two spaced passageway sections and from the two spaced through opening sections in said direction perpendicular to the direction of said longitudinal axis when said housing portions are in said open position.

9. In a read head for a luminometer comprising, a housing that supports a free end portion of optic fibers, and supports a transparent analytical line, which transparent analytical line houses moving test sample; wherein luminescence from said sample is transmitted though the transparent analytical line to the free end portion of the optic fibers for detection and analysis by the luminometer, the improvement comprising, a) a housing having a through opening with a longitudinal axis,
 b) said housing including a pair of housing portions joined together at a pivot, said housing portions being supported at said pivot on a support member for converging and diverging movement relative to said support member such that said housing portions are divergable away from each other a predetermined amount to a predetermined open position, and convergable from said open position to a closed limit position,
 c) said through opening being sized to confine an elongated analytical line when said housing portions are in said closed limit position, said through opening being positioned in said housing portions to split into two spaced through opening sections upon divergence of said housing portions to said predetermined open position to permit removal of said analytical line from the split sections of the through opening in a direction perpendicular to the direction of said longitudinal axis, and
 d) actuator means on said support member and said housing for actuating simultaneous converging movement or diverging movement of said housing portions relative to said support member.

10. The read head as claimed in claim 9 wherein said housing portions are hollow and a cylindrical core formed in two sections is disposed within said housing, one said core section being mounted to one said housing portion and the other said core section being mounted to the other said housing portion, said core sections defining a central passageway in alignment with said through opening for confinement of an analytical line in said central passageway when said housing portions are in said closed limit position, said core sections being divergable away from each other when said housing portions are diverged from each other, and wherein said central passageway is positioned such that divergence of said core sections splits said central passageway into two spaced passageway sections, to permit removal of said analytical line from said two spaced passageway sections and from said two spaced through opening sections in said direction perpendicular to the direction of the longitudinal axis when said housing portions are in said open position.

* * * * *